US00PP36272P2

(12) United States Plant Patent
van Dijk

(10) Patent No.: US PP36,272 P2
(45) Date of Patent: Nov. 26, 2024

(54) ANTHURIUM PLANT NAMED 'AN2142228'

(50) Latin Name: *Anthurium andreanum*
Varietal Denomination: AN2142228

(71) Applicant: ANTHURA B.V., Bleiswijk (NL)

(72) Inventor: Jan van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 18/607,499

(22) Filed: Mar. 17, 2024

(51) Int. Cl.
*A01H 5/02* (2018.01)
*A01H 6/00* (2018.01)

(52) U.S. Cl.
USPC ..... Plt./365

(58) Field of Classification Search
USPC ..... Plt./365, 368, 369
CPC ..... A01H 5/02; A01H 5/00; A01H 6/00
See application file for complete search history.

(56) References Cited

U.S. PATENT DOCUMENTS

PP30,966 P2 * 10/2019 Van Dijk ..... A01H 6/00
Plt./365

OTHER PUBLICATIONS

CPVO Register Version 4.20.1 retrieved on Jul. 9, 2024 at https://online.plantvarieties.eu/publicConsultationDetails?registerId=20222623&denomination=an2142228, 2 pp. (Year: 2024).*

UPOV Pluto 20240709 retrieved on Jul. 9, 2024 at https://plluto.upov.int/result, one page. (Year: 2024).*

* cited by examiner

*Primary Examiner* — June Hwu

(74) *Attorney, Agent, or Firm* — C. Anne Whealy

(57) ABSTRACT

A new and distinct cultivar of Anthurium plant named 'AN2142228', characterized by its upright to outwardly arching and uniform plant habit; freely clumping growth habit; bushy and dense plants; narrowly cordate dark green-colored leaves; freely flowering habit; inflorescences that are positioned within to slightly above the foliar plane on strong and erect scapes; broadly cordate dark reddish brown-colored spathes and dark reddish brown to dark red-colored spadices; and durable spathes that impart good inflorescence longevity.

2 Drawing Sheets

Figure 1:
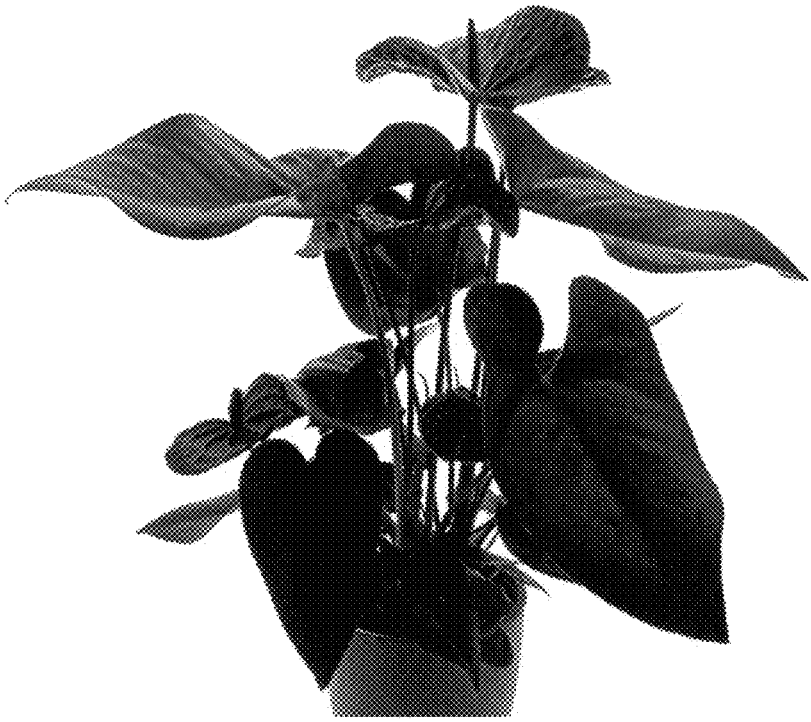

Botanical designation: *Anthurium andreanum.*
Cultivar denomination: 'AN2142228'.

STATEMENT REGARDING PRIOR DISCLOSURES BY INVENTOR and APPLICANT/ASSIGNEE

An European Community Plant Breeder's Rights application for the instant plant was filed by the Applicant/Assignee of the instant application, Anthura B. V. of Bleiswijk, The Netherlands on Nov. 22, 2022, application number 2022/2623. Foreign priority is not claimed to this application.

The Inventor and Applicant/Assignee assert that no sales, offers for sale or public distribution of the instant plant occurred more than one year prior to the effective filing date of this application.

Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of Anthurium plant, botanically known as *Anthurium andreanum* and hereinafter referred to by the name 'AN2142228'.

The new Anthurium plant is a product of a controlled breeding program conducted by the Inventor in Bleiswijk, The Netherlands. The objective of the breeding program is to create new vigorous Anthurium plants with durable, large and rugose dark reddish brown-colored spathes.

The new Anthurium plant originated from a cross-pollination made by the Inventor in November, 2013 in Bleiswijk, The Netherlands of a proprietary selection of *Anthurium andreanum* identified as code number 10-023679-0003, not patented, as the female, or seed, parent with *Anthurium andreanum* 'Anthuqclo', disclosed in U.S. Plant Pat. No. 33,338, as the male, or pollen, parent. The new Anthurium was discovered and selected by the Inventor as a single flowering plant within the progeny of the stated cross-pollination in a controlled greenhouse environment in Bleiswijk, The Netherlands in October, 2015.

Asexual reproduction of the new Anthurium plant by in vitro meristem propagation in a controlled environment in Bleiswijk, The Netherlands since July, 2017 has shown that the unique features of this new Anthurium are stable and reproduced true to type in successive generations of asexual reproduction.

SUMMARY OF THE INVENTION

Plants of the new Anthurium have not been observed under all possible combinations of environmental conditions and cultural practices. The phenotype may vary somewhat with variations in environment conditions such as temperature and light intensity, without, however, any variance in genotype.

The following traits have been repeatedly observed and are determined to be the unique characteristics of 'AN2142228'. These characteristics in combination distinguish 'AN2142228' as a new and distinct Anthurium plant:

1. Upright to outwardly arching and uniform plant habit.
2. Freely clumping growth habit; bushy and dense plants.
3. Narrowly cordate dark green-colored leaves.
4. Freely flowering habit.
5. Inflorescences that are positioned within to slightly above the foliar plane on strong and erect scapes.
6. Broadly cordate dark reddish brown-colored spathes and dark reddish brown to dark red-colored spadices.
7. Durable spathes that impart good inflorescence longevity.

Plants of the new Anthurium differ primarily from plants of the female parent selection in spadix color as plants of the new Anthurium have dark reddish brown to dark red-colored spadices whereas plants of the female parent selection have spadices that are green to creamy white in color. In addition, spadices of plants of the new Anthurium are straight in aspect whereas spadices of plants of the female parent selection are incurved.

Plants of the new Anthurium differ primarily from plants of the male parent, 'Anthuqclo', in spathe size and color as spathes of plants of the new Anthurium are larger than spathes of plants of 'Anthuqclo'; and additionally, spathes of plants of the new Anthurium are dark reddish brown in color whereas spathes of plants of 'Anthuqclo' are green in color.

Plants of the new Anthurium can also be compared to plants of *Anthurium andreanum* 'Anthfube', disclosed in U.S. Plant Pat. No. 30,966. In side-by-side comparisons, plants of the new Anthurium differ primarily from plants of 'Anthfube' in spadix color as plants of the new Anthurium have dark reddish brown to dark red-colored spadices whereas plants of 'Anthfube' have spadices that are green to creamy white in color. In addition, spadices of plants of the new Anthurium are straight in aspect whereas spadices of plants of 'Anthfube' are incurved.

BRIEF DESCRIPTION OF THE PHOTOGRAPHS

The accompanying photographs illustrate the overall appearance of the new Anthurium. The photographs show the colors as true as it is reasonably possible to obtain in colored reproductions of this type. Colors in the photographs may differ slightly from the color values cited in the detailed botanical description which accurately describe the colors of the new Anthurium.

The photograph on the first sheet (FIG. 1) is a side perspective view of a typical plant of 'AN2142228' grown in a container.

Figure 2:
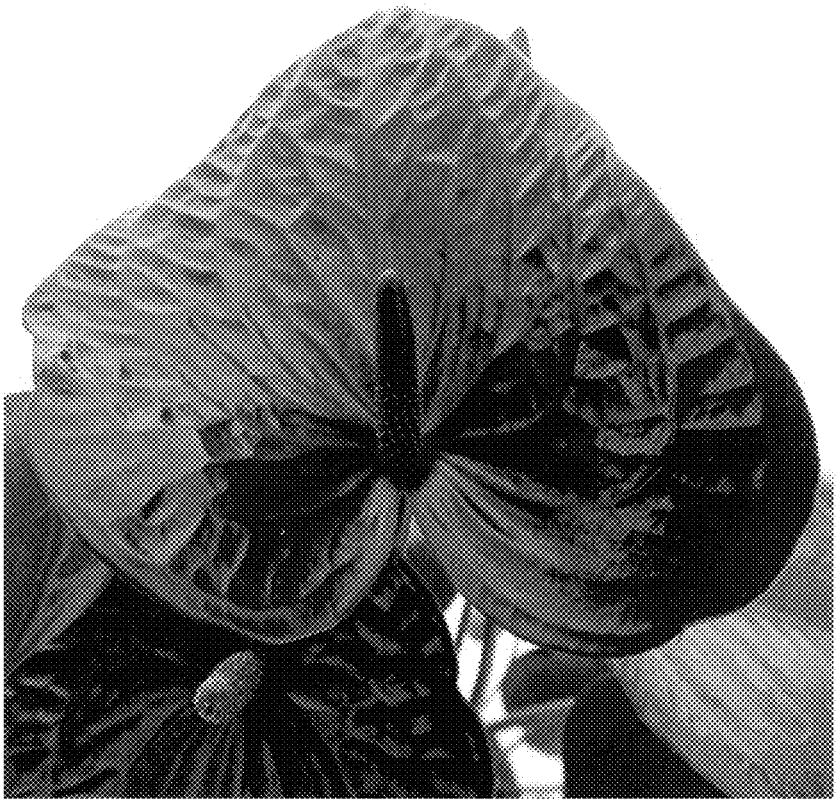

The photograph on the second sheet (FIG. 2) is a close-up view of typical inflorescences of 'AN2142228'.

DETAILED BOTANICAL DESCRIPTION

The aforementioned photographs and following observations and measurements describe plants grown in 14-cm containers in Bleiswijk, The Netherlands during the late autumn in a glass-covered greenhouse. Plants were grown under conditions and practices which approximate those generally used in commercial Anthurium production. During the production of the plants, day and night temperatures ranged from about 19° C. to 22.5° C. and light levels ranged from 100μmol to 200μmol. Plants were eleven months old when the photographs and the detailed description were taken. In the following description, color references are made to The Royal Horticultural Society Colour Chart, 2015 Edition, except where general terms of ordinary dictionary significance are used.

Botanical classification: *Anthurium andreanum* 'AN2142228'.

Parentage:

*Female, or seed, parent.*—Proprietary selection of *Anthurium andreanum* identified as code No. 10-023679-0003, not patented.

*Male, or pollen, parent.*—*Anthurium andreanum* 'Anthuqclo', disclosed in U.S. Plant Pat. No. 33,338.

Propagation:

*Type.*—By in vitro meristem propagation.

*Time to initiate roots, summer and winter.*—About two weeks at temperatures about 19° C. to 22.5° C.

*Time to produce a rooted young plant, summer and winter.*—About six to eight weeks at temperatures about 19° C. to 22.5° C.

*Root description.*—Medium in thickness, fibrous; typically pink in color, actual color of the roots is dependent on substrate composition, water quality, fertilizer type and formulation, substrate temperature and physiological age of roots.

*Rooting habit.*—Freely branching, medium density.

Plant description:

*Plant shape.*—Upright to outwardly spreading and uniform plant habit; overall shape, broadly obovate to broadly elliptic.

*Growth habit.*—Freely clumping habit with about five clumps per plant imparting a bushy and dense appearance; moderately vigorous growth habit and moderate growth rate.

*Plant height, from soil level to top of leaf plane.*—About 33.8 cm.

*Plant height, from soil level to top of inflorescences.*—About 39.4 cm.

*Plant diameter or spread.*—About 44.4 cm.

Leaf description:

*Arrangement.*—Alternate; simple; about four leaves per clump.

*Length.*—About 22.6 cm.

*Width.*—About 13.6 cm.

*Shape.*—Narrowly cordate.

*Apex.*—Acuminate to apiculate with mucronate apex.

*Base.*—Cordate.

*Margin.*—Entire; slightly to moderately and coarsely undulate.

*Texture and luster, upper and lower surfaces.*—Smooth, glabrous; moderately leathery; glossy.

*Venation pattern.*—Pinnate.

*Color.*—Developing leaves, upper surface: Slightly darker than a blend of 146A and 147A. Developing leaves, lower surface: Close to 148A. Fully expanded leaves, upper surface: Darker than a blend of 139A and N189A; venation, close to 139B. Fully expanded leaves, lower surface: Darker than 146A; venation, close to 146B.

*Petioles.*—Length: About 20.2 cm. Diameter: Distally, about 4 mm; proximally, about 5.5 mm. Strength: Strong. Texture and luster, upper and lower surfaces:

Smooth, glabrous; slightly glossy. Color, upper surface: Close to NN137A. Color, lower surface: Close to NN137C. Geniculum length: About 2.2 cm. Geniculum diameter: About 5 mm. Geniculum texture and luster, upper and lower surfaces: Smooth, glabrous; slightly glossy. Geniculum color, upper surface: Close to 146B slightly to strongly tinged with close to 177A and 177B. Geniculum color, lower surface: Close to 146B. Wing length: About 2.2 cm. Wing diameter: About 6 mm. Wing color: Close to 144A; towards the margins, close to 144B.

Inflorescence description:

*Inflorescence arrangement and flowering habit.*—Spathes with spadices held within and slightly above the foliar plane on strong and erect scapes; flowering structures arise from leaf axils; freely and continuous flowering year-round in controlled temperature greenhouses in The Netherlands; typically about seven developing and developed inflorescences per plant at one time; inflorescence development commences about 2.5 to 3.5 months after planting.

*Inflorescence longevity.*—Spathes maintain good substance for about two months on the plant; inflorescences persistent.

*Fragrance.*—None detected.

*Spathes.*—Length: About 14.3 cm. Width: About 13.3 cm. Shape: Broadly cordate, slightly irregular; flat to moderately concave. Apex: Broadly and abruptly acute with a mucronate tip. Base: Cordate. Margin: Entire; slightly to moderately and coarsely undulate. Aspect: At about 82.5° From the peduncle axis. Texture and luster, upper and lower surfaces: Smooth, glabrous; moderately leathery; glossy. Color When developing, front surface: Slightly lighter and more red than 187A; mucronate tip, close to 146B. When developing, rear surface: Close to a blend of 175A and 175B slightly tinged with close to 146A; mucronate tip, close to 146C. Fully developed, front surface: Close to 200A slightly tinged with close to N186C; mucronate tip, close to 146C; with subsequent development, color becoming closer to 200A to 200B. Fully developed, rear surface: Close to 175A slightly to moderately tinged with close to 146A and 146B; mucronate tip, close to 146C and 146D; with subsequent development, color becoming closer to 175A slightly to moderately tinged with close to 146B.

*Spadices.*—Length: About 4.8 cm. Diameter: About 1 cm. Shape: Columnar, slightly tapering towards the apex; apex, obtuse; base, obtuse; in cross-section, rounded. Aspect: About 75° From spathe axis and about 10° from the peduncle axis. Color: Immature: Close to 200B. Mature: Close to 185A. Flowers: Type: Hermaphroditic. Quantity per spadix: Numerous, about 200. Height: Less than 0.5 mm. Diameter: About 2.5 mm. Shape: Roughly square. Anther color: Close to 185A. Pollen amount: Moderate to abundant. Pollen color: Close to 155B. Stigma color: Close to 156A.

*Scape.*—Length: About 26.5 cm. Diameter: About 5 mm. Strength: Strong. Aspect: About 30° From vertical. Color: Slightly darker than 146A tinged with close to 152A; with subsequent development, proximally, becoming closer to 143A and 143B and distally, closer to 200C.

*Seed and fruit.*—To date, seed and fruit development has not been observed on plants of the new Anthurium.

Pathogen & pest resistance: To date, plants of the new Anthurium have not been observed to be resistant to pathogens or pests common to Anthurium plants.

Temperature tolerance: Plants of the new Anthurium have been observed to be tolerant to high temperatures about 30° C. and to be hardy to USDA Hardiness Zone 10.

It is claimed:

1. A new and distinct Anthurium plant named 'AN2142228' as herein illustrated and described.

* * * * *